United States Patent
Klimov et al.

(10) Patent No.: US 8,334,143 B2
(45) Date of Patent: Dec. 18, 2012

(54) FLUORESCENT NANOSCOPY METHOD

(75) Inventors: Andrey Alexeevich Klimov, Puschino (RU); Dmitry Andreevich Klimov, Puschino (RU); Evgeniy Andreevich Klimov, Puschino (RU); Tatiana Vitalyevna Klimova, Puschino (RU)

(73) Assignee: Stereonic International, Inc., Short Hills, NJ (US)

( * ) Notice: Subject to any disclaimer, the term of this patent is extended or adjusted under 35 U.S.C. 154(b) by 0 days.

(21) Appl. No.: 13/366,813

(22) Filed: Feb. 6, 2012

(65) Prior Publication Data

US 2012/0133740 A1    May 31, 2012

Related U.S. Application Data

(63) Continuation of application No. 12/891,420, filed on Sep. 27, 2010, now Pat. No. 8,110,405, which is a continuation of application No. 11/920,661, filed as application No. PCT/RU2006/000231 on May 5, 2006, now Pat. No. 7,803,634.

(30) Foreign Application Priority Data

May 18, 2005   (RU) ................................ 2005115052

(51) Int. Cl.
   *G01N 21/76*       (2006.01)
   *G01N 1/00*        (2006.01)

(52) U.S. Cl. ........ 436/172; 436/164; 436/174; 977/840; 977/881; 977/868; 977/869; 356/401

(58) Field of Classification Search .................. 436/172, 436/164, 174; 977/840, 881, 868, 869; 356/401
See application file for complete search history.

(56) References Cited

U.S. PATENT DOCUMENTS

| | | |
|---|---|---|
| 5,635,608 A | 6/1997 | Haugland et al. |
| 6,953,927 B2 | 10/2005 | Quake et al. |
| 7,110,118 B2 | 9/2006 | Ünlü et al. |
| 7,224,452 B2 | 5/2007 | Hell |
| 7,476,787 B2 | 1/2009 | Thomas et al. |
| 7,538,893 B2 | 5/2009 | Hell et al. |

(Continued)

FOREIGN PATENT DOCUMENTS

DE              444 5214 A1      6/1996
(Continued)

OTHER PUBLICATIONS

N. Fang et al., "Imaging properties of a metalmaterial superlens," App Phys Let 2003, vol. 82, 2, pp. 161-163.

(Continued)

*Primary Examiner* — Brian J Sines
(74) *Attorney, Agent, or Firm* — Pauley Petersen & Erickson

(57) ABSTRACT

A method for analysis of an object dyed with fluorescent coloring agents. Separately fluorescing visible molecules or nanoparticles are periodically formed in different object parts, the laser produces the oscillation thereof which is sufficient for recording the non-overlapping images of the molecules or nanoparticles and for decoloring already recorded fluorescent molecules, wherein tens of thousands of pictures of recorded individual molecule or nanoparticle images, in the form of stains having a diameter on the order of a fluorescent light wavelength multiplied by a microscope amplification, are processed by a computer for searching the coordinates of the stain centers and building the object image according to millions of calculated stain center co-ordinates corresponding to the co-ordinates of the individual fluorescent molecules or nanoparticles. Two-dimensional and three-dimensional images are provided for proteins, nucleic acids and lipids with different coloring agents.

12 Claims, 2 Drawing Sheets

U.S. PATENT DOCUMENTS

| | | | |
|---|---|---|---|
| 7,764,369 | B2 | 7/2010 | Hell et al. |
| 7,767,414 | B1 | 8/2010 | Smith et al. |
| 7,785,505 | B2 | 8/2010 | Papazoglou |
| 7,816,654 | B2 | 10/2010 | Baer |
| 2004/0227694 | A1 | 11/2004 | Sun et al. |
| 2007/0178305 | A1 | 8/2007 | Papazoglou |
| 2008/0068588 | A1 | 3/2008 | Hess et al. |
| 2008/0068589 | A1 | 3/2008 | Hess et al. |
| 2008/0070322 | A1 | 3/2008 | Hess et al. |
| 2008/0070323 | A1 | 3/2008 | Hess et al. |
| 2008/0111086 | A1 | 5/2008 | Betzig et al. |
| 2009/0045353 | A1 | 2/2009 | Klimov et al. |
| 2009/0206251 | A1 | 8/2009 | Hess et al. |
| 2011/0175982 | A1 | 7/2011 | Klimov et al. |

FOREIGN PATENT DOCUMENTS

| | | |
|---|---|---|
| RU | 2166201 C1 | 4/2001 |
| SU | 1493673 A1 | 7/1989 |

OTHER PUBLICATIONS

N. Fang et al., "Regenerating evanescent waves from a silver superlens," Optics Express 2003, vol. 11 No. 7, pp. 682-687.

National Institute of Standards and Technology (NIST), "Optical Microscopes Enter the Nano Age," Betterhumans Newsletter © 2002-2005, 2 pages.

E. Mei et al., "Direct visualization of nanopatterns by single-molecule imaging," App Phys Let 2005, 86:043102.

E. Betzig, "Proposed method for molecular optical imaging," Optics Letters, Feb. 1, 1995, vol. 20, No. 3, pp. 237-239.

M. Gordon et al., "Single-molecule high-resolution imaging with photobleaching," PNAS 2004, Apr. 27, vol. 101, No. 17, pp. 6462-6465.

Xiaohui Qu et al., "Nanometer-localized multiple single-molecule fluroescence microscopy," PNAS 2004, Aug. 3, vol. 101, No. 31, pp. 11298-11303.

Molecular Probes, Inc., Molecular Probes ProLong Antifade Kit (P7481) Product Information Sheet 2005, MP07481, 3 pages.

E. Fureder-Kitzmuller et al., "Non-exponential bleaching of single bioconjugated Cy5 molecules," Elsevier Chemical Physics Letters 2005, No. 404, pp. 13-18.

V. Westphal et al., "Nanoscale Resolution in the Focal Plane of an Optical Microscope," APS 2005, Apr. 15, PRL 94(14), 143903, 4 pages.

T. Lacoste et al., "Ultrahigh-resolution multicolor colocalization of single fluorescent probes," PNAS, Aug. 2000, vol. 97, No. 17, pp. 9461-9466

M. Gustafsson, "Nonlinear structured-illumination microscopy: Wide-field Fluorescence imaging with theoretically unlimited resolution," PNAS Sep. 2005, vol. 102, pp. 13081-13086.

A. Lee et al., "Single-Molecule Enzymology of Chymotrypsin Using Water-in-Oil Emulsion," Biophys J., Jun. 2005, vol. 88, pp. 4303-4311.

Enderlein et al., "Statistics of Single-Molecule Detection," J. Phys. Chem B 1997, vol. 101, pp. 3626-3632.

M. Wallace et al., "Combined single-molecule force and fluorescence measurements for biology," J of Biology, Apr. 2003, vol. 2:4, 5 pages.

K. Weston et al., "Room-temperature fluorescence characteristics of single dye molecules absorbed on a glass surface," J of Chem Phys, Nov. 1998, vol. 109, pp. 4303-4311.

S. Hell et al., "Concepts for nanoscale resolution in fluorescence microscopy," Current Opinion in Neurobiology 2004, vol. 14, pp. 599-609.

M. Cheezum et al., Quantitative Comparison of Algorithms for Tracking Single Fluorescent Particles, Biophys J., Oct. 2001, vol. 81, pp. 2378-2388.

R. Haugland, "Photoactivatable ("Caged") Probes," Molecular Probes Handbook 1992-1994, pp. 181-184.

G. J. Schutz et al., "Single-molecule Microscopy on Model Membranes Reveals Anomalous Diffusion," Biophys J., Aug. 1997, vol. 73, pp. 1073-1080.

S. Sund et al., "Cell Membrane Orientation Visualized by Polarized Total Internal Reflection Fluorescence," Biophy J., Oct. 1999, vol. 77, pp. 2266-2283.

R. Heintzmann et al., "Breaking the resolution limit in light microscopy," Briefings in Funcational Genomics and Proteomics 2006, vol. 5, No. 4, pp. 289-301.

A. Egner et al., "Fluorescence nanoscopy in whole cells by asynchronous localization of photoswitching emitters," Biophys J BioFAST, Jul. 2007, 18 pages.

C. Middendorff et al., "Isotropic 3D Nanoscopy based on single emitter switching," Optics Express, Dec. 2008, vol. 16, No. 25, 15 pages.

S. Manley et al., "High-density mapping of single-molecule trajectories with photoactivated localization microscopy," Nature Methods, Jan. 13, 2008, 3 pages.

www.invitrogen.com/site/us/en/home/References/Molecular-Probes, Molecular Probes, The Handbook, Photoactivatable Reagents, Including Photoreactive Crosslinkers and Caged Probes—Section 5.3, 2001, 14 pages.

M. Rust et al., "Sub-diffraction-limit imaging by stochastic optical reconstruction microscopy (STORM)," Nature Methods, Aug. 9, 2006, 3 pages.

M. Fernandez-Suarez et al., "Fluorescent probes for super-resolution imaging in living cells," Nature Reviews, Molecular Cell Biology, Dec. 2008, vol. 9, pp. 929-943.

E. Betzig et al., "Imaging Intracellular Fluorescent Proteins at Nanometer Resolution," Science, Sep. 15, 2006, vol. 313, pp. 1642-1645.

A. Sharonov et al., "Wide-field subdiffraction imaging by accumulated binding of diffusing probes," PNAS 2006, Dec. 12, vol. 103, No. 50, pp. 18911-18916.

Stefan Hell, "Far-Field Optical Nanoscopy," Science 2007, May 25, vol. 316, pp. 1153-1158.

J. Vogelsang et al., "Controlling the fluorescence of ordinary oxazine dyes for single-molecule switching and superresolution microscopy," PNAS 2009, vol. 106, No. 20, pp. 8107-8112.

M. Bates et al., "Multicolor Super-Resolution imaging with Photo-Switchable Fluorescent Probes," Science, Sep. 21, 2007, vol. 317, pp. 1749-1753.

C. Waterman-Storer et al., "New Directions for Fluorescent Speckle Microscopy," Current Biology, Sep. 2002, vol. 12, pp. 633-640.

FLUORESCENT NANOSCOPY METHOD

CROSS REFERENCE TO RELATED APPLICATIONS

This application is a continuation of U.S. patent application Ser. No. 12/891,420, filed on 27 Sep. 2010, and issued as U.S. Pat. No. 8,110,405, which is a continuation of U.S. patent application Ser. No. 11/920,661, filed on 19 Nov. 2007, and issued as U.S. Pat. No. 7,803,634, which is a National Phase Patent Application of PCT/RU2006/000231. The co-pending parent application is hereby incorporated by reference herein in its entirety and is made a part hereof, including but not limited to those portions which specifically appear hereinafter.

BACKGROUND OF THE INVENTION

1. Field of the Invention

This invention relates to equipment for scientific research, and lens fluorescence microscopes in particular, that are used for obtaining images of fluorescent objects immobilized on a glass. This invention also relates to a computerized fluorescent-microscopically method of reconstructing images of objects with resolution up to several nanometers (nm).

2. Discussion of Related Art

There are known optical microscopes which can create zoomed images of an object with object lenses that can show two spots on an object separately only when the distance between them is more than so called diffraction limit. This limit can be calculated using following formula: $r=0.61\lambda/A$ (1), where $\lambda$ is light wavelength for light collected by object lens with aperture $A=n*\sin(\phi)$, n is a refraction index of substance which surrounds object spots, $\phi$ is an angle between object lens axis and extreme rays which fall into object lens and are detected in detector. Now, different types of devices are used for fluorescent microscopy by object lenses. Powerful arc-lamps, incandescent lamps, laser or sun light can be light sources for the microscope. Fluorescence starts in all dye molecules are present in a lighted area. The area is lighted through the object lens using a light-dividing dichroic mirror that lets exciting light to fall on the object and reflects fluorescence light to the detector. The second type of lighting occurs by sending laser light from the side and lights the object all the way down or through an object glass at a total internal reflection angle. In this case, light reaches a depth of only 0.3 of light wavelength from border between glass and an object which has a refraction index lower than glass. Object fluorescent light is collected by an object lens and sends an object image for visual observation and registration by a photomultiplier, a photographic tape or a digital video-camera. The main disadvantage of all existing lens microscopes is that they have a limit of resolution for two neighboring spots and the limit can be calculated according to the above formula (1).

Recently, microscopy using super lenses made from silver film has been developed. A film thickness less than 50 nm can assure resolution of two spots on a distance of approximately 50 nm from each other. (N. Fang and X. Zhang, Imaging properties of a metamaterial superlens, 2003, App phys Let v. 82, 2, 161-163; Nicholas Fang, Zhaowei Liu, Ta-Jen Yen, and Xiang Zhang Regenerating evanescent waves from a silver superlens, 2003, OPTICS EXPRESS, Vol. 11, No. 7, 682-687). Use of such microscopes on biological objects is unclear. The present microscope model has a resolution several times lower than a resolution of the device that we propose.

There are devices with a maximum resolution better than 1 nm, for example, electronic, tunnel, and atomic-force microscopes that have not only real advantages but also serious disadvantages, such as: complexity and expensiveness of their design and work with objects; lack of opportunity to receive a color image for distinguishing molecules of different types; objects that usually should be dried and treated with substances which change the mutual layout of different parts of the object. Atomic and tunnel microscopes also do not detect structures inside the object; only one spot can be detected at a time and a scanning speed does not overcome 1 square micron per min; and an end of the needle easily becomes dirty and does not then reach an object surface.

There is also a device, where object fluorescence is excited by laser through a pinhole on the tip of a glass fiber. The fiber is moved by drives in three directions to position an end of the fiber near light-reflecting, light-diffusing or covered with fluorescent molecules surface. This type of microscope does not use lenses and permits obtaining images with resolution ten times better than the resolution of common optical microscopes. These results can be reached only when the pinhole on the tip of glass fiber is much less in diameter than in light wavelength. The light comes onto an object with a depth much shorter than a light wavelength. Practically all light returns back into the glass fiber, except that part which was captured by objects from outside of the hole. Fluorescence, light-diffusion, and reflected light strength, captured in the object near the hole, are measured by a photomultiplier. The image of an object surface is reconstructed by a computer, which gathers information about the strength of measured light and data on an end of glass fiber coordinates. The main disadvantages of this system are: a need to use expensive high-precision and fast-acting mechanic units, responsible for moving of glass fiber against object; production of glass fiber with an end hole less than 50 nm in diameter is very expensive, complex and difficult for duplicating; the hole is easily dirtied and is not able to then reach an object surface; only an insignificant part of light can leave the fiber through the hole with a diameter less than light wavelength; increases of light intensity leads to overheating and destruction of the fiber end; it is impossible to detect fluorescence in the areas of the object which are not accessible by glass fiber; and only one spot can be detected at a time, and surface scanning speed does not exceed 1 square micron per minute.

One more new microscope type scans an object surface with several light beams simultaneously. National Institute of Standards and Technology (NIST) issued a grant for 5 years research work on creation of this microscope (http://www-.betterhumans.com/News/news.aspx?articleID=2005-02-11-4, "Optical Microscopes Enter the Nano Age. Hybrid system being developed to image and measure features smaller than the wavelength of visible light".) The article states that a 40 nm nanoparticle can be distinguished using this method. There are no indications of authors being successful in distinguishing two separate particles located on a distance less than 40 nm from each other. It is not clear from presented drawings and explanations how this method will allow distinguishing two particles on distance less than $r<0.61\lambda/A$ between them and the suggested device will likely not reach resolution of object details, located on a distance much shorter than light wavelength.

One method of using common fluorescent microscope (Erwen, A Sharonov, J H Ferris, R M Hochstrasser: Direct visualization of nanopatterns by single-molecule imaging. App Phys Let 2005, 86: 043102) can be thought of as relevant to this invention. The main idea of this method is that a sample, a light film of polymer with free open spherical cells 1 micron in diameter, is dyed with very low concentration of fluorescent peptide. Such concentration allows to observe separate peptide molecules which can migrate in Brownian motion inside the hollow of spheres. The sample is lighted through an object glass by a laser beam. A lightning angle is equal to a total internal reflection angle. A laser beam excites fluorescence in a 150-200 micron layer of the sample near the glass. A location of several tens of molecules of fluorescing peptide, each of which was dyed by simultaneously fluorescing molecules, was detected by a high-sensitivity video camera (Roper Scientific, Cascade 512F with electrons multiplier built in CCD) in 500 sequential frames. Each frame was recorded to computer memory. Each image contained many spots of approximately 0.5 microns in diameter multiplied on a system zoom value. All these images were added to each other and a resultant image had a resolution not exceeding a resolution of a common fluorescent microscope. Main disadvantages of this system are: there is no information in the article about opportunity to calculate a location of detected spot centers and to generate an image on the basis of these spots with resolution higher than a diffraction limit (see formula 1); approaches to selective dyeing of object structures are not described in the article; and there is no description of solving that after dyeing, substances lose color in the process of detecting non fluorescing peptide molecules staying in an observation area. This will make the solution more thick and will not allow replacing such molecules with new fluorescing ones. This does not allow obtaining larger quantity of frames than 500. These large quantities are needed to receive image with resolution higher than allowed by a diffraction limit (see formula 1).

SUMMARY OF THE INVENTION

Researching of biological objects, for example muscles, includes the fact that many different types of molecules are located much closer than the resolution of common optical microscopes which create a zoomed image of the object by an object lens in a plane of a recorder, eye, photo or video camera. The diffraction limit of microscope resolution (formula 1) limits the resolution in microscopes with simultaneous observation of all spots in the observation area and in microscopes with sequential observation of all spots of an object by a light ray being focused on one spot (confocal and other types of scanning lens microscopes). That is why it is good if all the advantages of optical microscopes and used methods of selective dyeing of different types of molecules in a vision area are united with such improvement of resolution, which would allow separate observation of molecules located less than 10-20 nm from each other.

This invention provides methods of dyeing objects, preparing objects for research, computer analysis of results. This procedure will allow receiving an object image with resolution higher than 20 nm. This will turn a fluorescent microscope into a "nanoscope". This task is solved by making multiple pictures of low dyed objects, (all fluorescing molecules in the objects are seen separately as spots with a diameter of $2r=1.22\lambda/A$, having different location on tens of thousands of sequential frames). Further, all these frames are used to calculate locations of centers of all detected spots (the locations correspond with actual coordinates of fluorescing molecules). Then 3-D reconstruction of all dye molecule locations is performed. Resolution is comparable with a fluorescing molecule size. Different structures of the object can be dyed in different colors. Fluorescent nanoscopes can be based on standard modules, used in fluorescent microscopy. This invention comprises various modules: an optical system for visual observation and transmitting of object image to digital video camera. The video cameras should be able to detect and digitize images of separate fluorescing molecules and nanoparticles with low background noise level. A second module of the system is a computer for recording and analyzing images. A third component is a sample holder, located opposite to objective lens. A fourth component is a set of changeable suppressing color filters for picking up light of sample fluorescence. The nanoscope should be equipped with two light sources installed aside from a sample holder. An installation angle should assure lighting of an entire slice of the sample on full depth or in a layer less than 150 nm near the glass. Fluorescent molecules in this layer can absorb energy of light waves, flowing through the border when lighted on a total internal reflection angle. Observation objects should be preliminary dyed in a solution with a saturating concentration of caged dye which starts fluorescing only when a UV light pulse separates blocking fluorescence groups from dye molecules. Superfluous dye should be carefully washed out. It is very hard to assure stability of molecular structures for a long time far from covering a glass and a prism glass holding the object. This is true for objects observed exactly in a fresh flushing solution. That is why the best resolution of a nanoscope can be received only for those layers of the object which are located on the distance not more than 150 nm from the prism glass. This is the depth which light reaches when falling on the boundary surface at a total internal reflection angle. In case of observing a dead preserved object it is usually possible to observe the object during many hours. Different structures, located near a base glass are almost an absolute immovable. They keep their location because of multiple stable mutual connections and connections with the base glass. They are immovable in spite of the fact that nearly 80% of volume is occupied with an aqueous solution of different salts. Gaps on glass edges should be hermetically sealed (for example, with paraffin) to avoid drying of the solution.

3-D nanoscopy requires total immobility of the object and its parts against an objective lens. That is why the object, after being dyed with caged dye and flushed, should be treated with dehydrating solutions and placed into a polymer non-fluorescent substance (for example, epoxy). Microscopic sections of the object of several microns thickness can be used for 3-D reconstruction of the object with 10-20 nm resolution in all three dimensions. Such an object contained in a solid substance can be lighted as it is done in common fluorescent microscopy. Only an improvement of an additional flashlamp should be used in order to turn several hundred non-fluorescing molecules into fluorescing in each frame. For both, object in liquid and object in polymer film, a UV flashlamp with $\lambda<360$ nm periodically lights the object, dyed with non-fluorescing dye, and each time turns several hundred (and even a thousand) of non-fluorescing molecules into fluorescing ones by photolysis of special chemical groups blocking fluorescence. The laser constantly lights the object and excites fluorescence of newly formed fluorescent molecules with such intensity, that each of them will send several tens of thousands of light quanta in part of a second. Molecules will lose color after registration of its fluorescence on a digitized frame with low background noise level. Cycling of fluorescent molecules generation, their excitation, registration and losing color can be repeated tens of thousands of times. Each time new fluorescence molecules will be generated, detected and will lose color. Not converted non-fluorescent molecules will not lose color because they do not absorb laser light. Tens of thousands of frames can be detected using this method. Hundreds and even thousands of fluorescing molecules can be detected on each frame. It will allow calculation of locations of all tens of millions of fluorescing molecules covering surfaces of all structures, located in a field of vision. Dyes with different active groups can be used for dyeing structures of different nature in different colors. Active groups can link to either proteins, either nucleic acids, either fats, etc. (one suggested method name is color nanoscopy).

The second modification of a nanoscopy method is based on the fact that the Brownian motion of very bright fluorescing and color loss-resistant nanoparticles is possible inside most parts of volume of a biological sample with penetrated membranes, filled with salt solution. Nanoparticles are presented by phycobiliprotein molecules or fluorescing micro spheres 10-40 nm in diameter. This motion can be regulated by electrophoresis with current, provided by several pairs of interlacing electrodes. Current directs the particles motion in different directions, so they scan all accessible volume. If several hundreds of the same, or replaced with those which are out of lighted area, fluorescing particles that are moving on the distance more than 1-2 microns from each other are detected in each frame, then it is possible to calculate their location with several nm accuracy, as coordinates of centers of corresponding spots. Coordinates from all frames can be used for finding out all locations where particles can appear over a long time period. It indicates all volume that is occupied with liquid. Part of the volume, where particles were not able to be present, can be considered to be occupied with dense structures of different origin, peptides, chromosomes, parts of not damaged membranes, etc. Possible fluctuations of a particle location can enlarge a spot size a little, but a spot center location can be considered as an averaged coordinate of the particle in the object. It should be noted, that particles with positive charge, negative charge, and neutral particles can visit different areas of the object because they interact with local charges of bio-structures, and that is why this method can be useful for studying surface charges of object structures, such as a suggested name of the method being monochrome nanoscopy.

Both suggested methods can assure a nanoscope resolution up to several nm, depending not from resolving power (formula 1), but from intrinsic mobility of structures in an observed part of the object during a long time period. A second factor is a proportion between noise and signal in video data. Both factors can be adjusted by various modifications of presented methods. For example, some bright shining key fluorescing particles can be introduced into the object. Then coordinates of replacing particles can be calculated taking into account movement in a vision area of key particles rigidly connected with the object. Such approach allows reaching 2-D distinguishing parts of the object, located on the distance of several nm.

It should be noted that some parameters of fluorescing particles images, a diameter of spots and light intensity distribution along a section of each spot, can change as particle distances from a focal plane of a microscope object lens. That is why it is suggested to perform a calculation of these parameters in order to calculate a third coordinate of the shining particle. It is suggested to project an object image on two video-cameras. This will improve precision of the third coordinate definition. The light rays are divided in two rays after the object lens. Video-cameras are located so that two neighboring focal planes of the object would be projected on them through one object lens. Light intensity distribution for each particle will be different when detected by different cameras. It can be scaled depending from the third coordinate and used to create 3-D images of the objects. FIG. 3 shows an illustration of 3-D nanoscopy foundations. A diameter and intensity of spots from fluorescing particles which are projected on CCD, depends from a distance between the particle and the object lens. Two cameras, focused on different focal planes, show one particle with different diameters and a different intensity distribution along diameters. The diagrams in the upper right corner of the figure illustrate differences between diameters and a distribution of intensity along diameters depending from cameras and a fluorescing particles location.

A nanoscope in some cases can be helpful in finding centers of spots which are created by fluorescing particles in two-three different wavelengths and same exciting status. It can be done by separating light dichroic mirrors that pass light with one wavelength to one camera and reflect light with the other wavelength to the other camera. Thus, this invention allows to reconstruct simultaneously with a nano resolution location of several different types of object molecules when having these molecules dyed with dyes having different emitting wavelengths, and this will allow enlarged quantities of simultaneously seen and detected separately spots from fluorescing particles due to the fact that they can be seen separately in waves of different lengths, even if corresponding spots of different colors are seen interfering.

It can be very useful if described methods of nanoscope work are combined with an additional changing of caged non-fluorescing molecules into fluorescing ones. This can be done by chemical reactions or different physical influences which will separate groups which block fluorescence. Examples of such reactions are ATP reactions, esterase influence, peroxidation, radioactive transformation, etc. Fluorescing molecules, created as result of such modifications, can be excited by laser and detected with video-cameras, used for calculating coordinates of an object structure surface according to above described methods. Their coordinates can be calculated as centers of appropriate spots on video frames. Then their images can be "overlapped" on an earlier reconstructed image of the object. They will show a location of reaction active groups of the object. Resolution of such image will be better than 20 nm.

This invention is described in the attached claims, and can be modified with different methods, not stepping aside from basic ideas of this invention.

Operation of the device in nanoscope mode can be altered by using a fluorescence microscope in the normal mode. This mode gives opportunity of direct visual observation of the object in situ with common resolution (formula 1). It also gives an opportunity to detect an image with a digital video-camera of very high sensitivity and to transmit it to computer memory. Then these frames will be analyzed to measure geometric parameters and light intensity in different areas of the frame. This can be used, for example, during bioluminescent and chemoluminescent research.

BRIEF DESCRIPTION OF THE DRAWINGS

The drawings show how a fluorescent microscope can be modified to implement a nanoscopy method according to this invention.

DETAILED DESCRIPTION OF THE INVENTION

Figure 1:
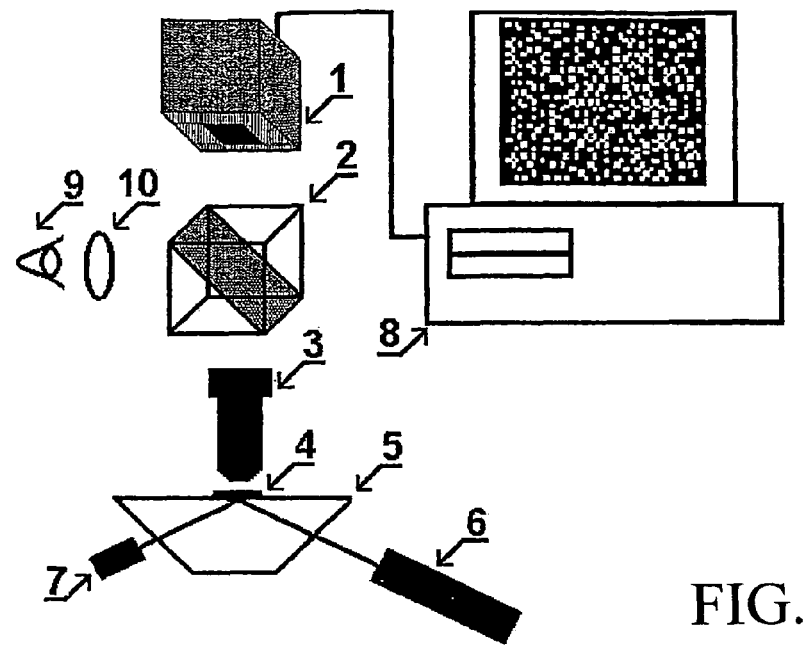
FIG. 1 is a fluorescent microscope-nanoscope equipped with one monochrome video camera.
Figure 2:
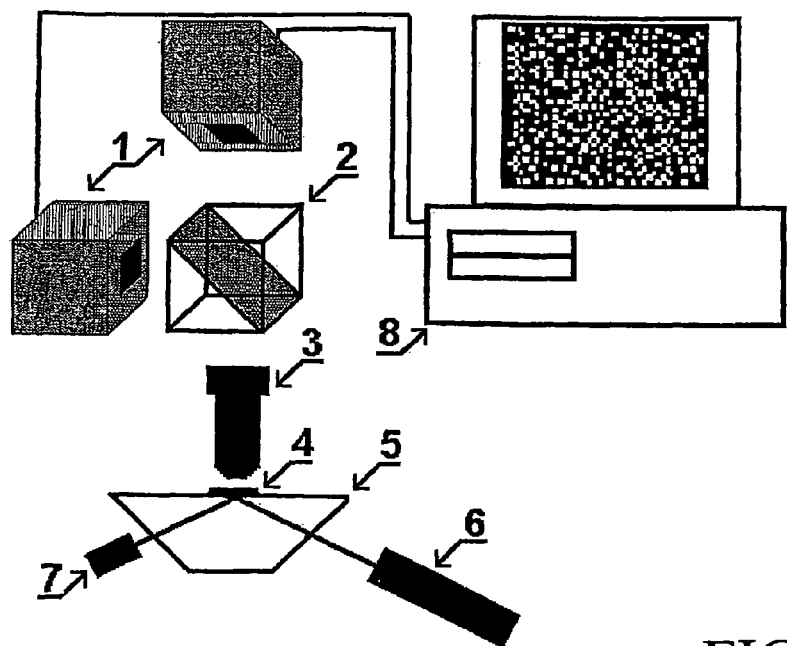
FIG. 2 is a fluorescent microscope-nanoscope equipped with two monochrome video cameras.
Figure 3:
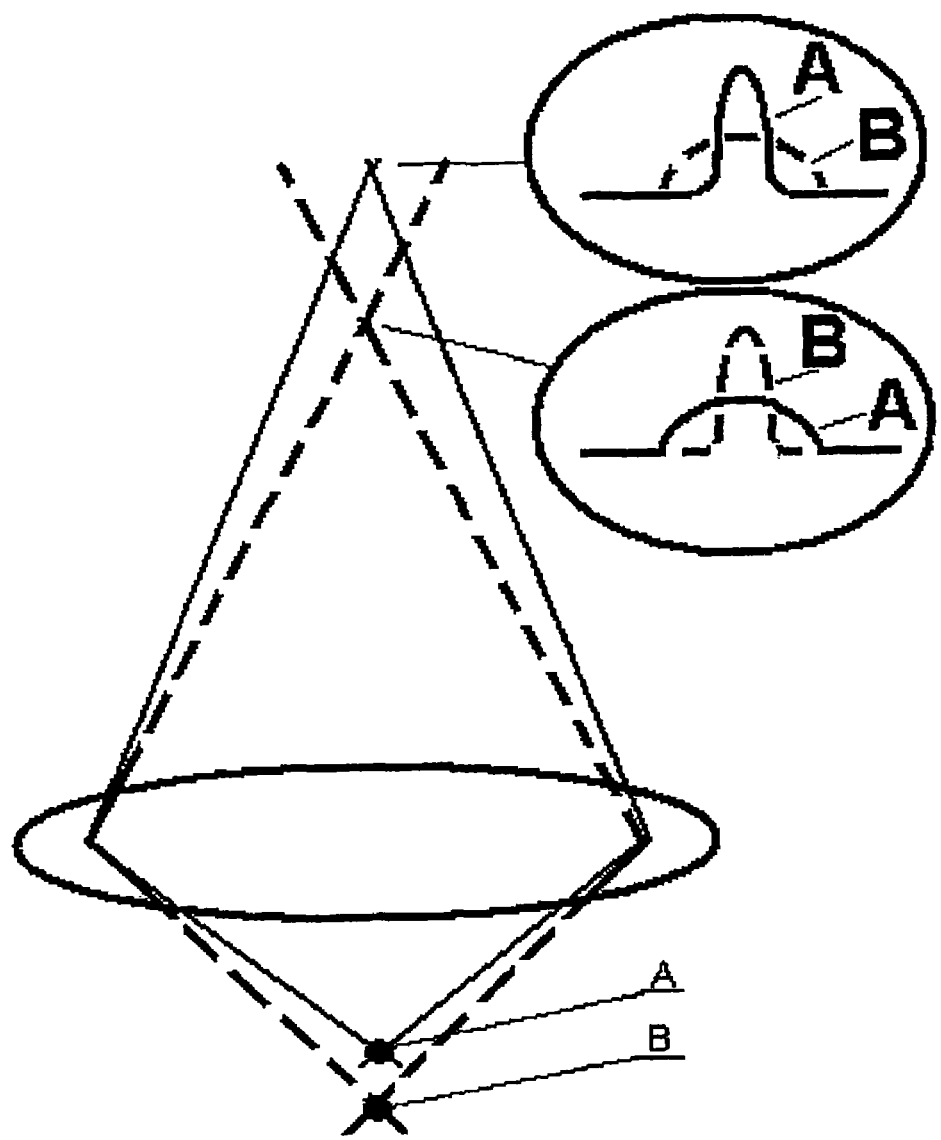
FIG. 3 shows an illustration of 3-D nanoscopy foundations.

The fluorescent microscope-nanoscope, as it is shown on FIGS. 1 and 2, is equipped with: one (FIG. 1) and two (FIG. 2) monochrome video-cameras (1) with digital output and suppressing color-filters, located opposite to their sensors (CCD). These color-filters pass only fluorescent light to cameras. A microscope is also equipped with a light dividing removable prism (2); object lens (3) with zoom up to 100× and an aperture up to A=1.4. Object (4) is pressed down to glass object holder (5) which is beveled in the form of truncated prism edges. The device also has laser (6) with lens system for exciting fluorescence through prism planes; with a pulse UV-source (7) with a lens system for photolysis of blocking fluorescence groups, present on dye molecules. Another important part is computer (8) with software for recording and working with digitized images. This software is also used for control of a power source, and providing energy for UV pulses and electrophoresis device. Eye lens (10) (FIG. 1) is used for visual observation (9). Unit should be placed into soundproof cabinet, placed on an anti-vibration table. The device, providing power to electrophoresis electrodes which direct movement of mobile fluorescing nanoparticles inside the object, filled with salt solution, will be described separately.

This is an example of receiving an image with a nanoscope which uses high sensitivity cameras Cascade 1K, such as produced by Photometrics, or cameras SIS1_t285EM, or produced by Theta-system. SIS1_t285EM cameras are equipped with CCD TC285SPD, produced by Texas Instruments, with electrons multiplier which is included in CCD crystal. It has a quantum effectiveness up to 63%, 1004 active horizontal square pixels with side of 8 microns in 1002 lines on a photosensitive square of approximately 8×8 mm. If an object image is projected directly to CCD of a video-camera by a 100× object lens, then square on the object, lighted with a laser and its lens system, should be a little bit larger than 80×80 microns. Each CCD pixel corresponds with an object square of 80×80 nm. Each shining particle or molecule is seen on the object as a spot with a diameter of $2r=1.22\lambda/A$, which is near 560 nm. It will be projected to a CCD square with a diameter near 7 pixels. The average distance between chaotically spread particles in each frame should be more than 2000 nm. In this case, practically all of them will be seen separately. In this case, at least 40×40=1600 spots can be simultaneously projected to CCD in each frame in such a manner, that they will be observed separately. Different methods can be used to reach a concentration of simultaneously fluorescing particles. First, it is possible to dye an object with brightly fluorescing particles in low concentration. This will allow them to move in an observation area in a Brownian motion and they can be additionally moved with an electrophoresis current. Current is provided with several pairs of electrodes in such manner that it will direct particles to move in different directions. Secondly, the object can be dyed with special dyes like 5-carboxyfluorescein-bis-(5-carboxymetoxy-2-nitrobenzil) ester, beta-alanin-carboxylamid, suxynimidil ester (CMNB-caged carboxyfluorescein, SE), fabricated by Molecular Probes, USA. After lighting with a UV flash with a wavelength of 310-365 nm (with a previously adjusted exposition) approximately 1000-1600 molecules of this non-fluorescing dye in an observation area will loose special groups which block fluorescence. Such molecules are able to produce several thousands quanta of green light when lighted with blue light. After this they will lose color. When an objective lens aperture is A=1.1-1.3, more than 10% of light from each fluorescing particle will be transmitted to a video-camera and participate in formation of the spot, covering near 40 pixels of CDD. Light intensity in the center of the spot is up to 100 quanta. This is enough to receive a video signal with quite a satisfactory proportion of signal and noise (when using the above mentioned cameras). This proportion will allow calculating coordinates of a spot center with resolution higher than 20 nm. This dye does not absorb laser light and lose color while groups which block fluorescence are linked to it. That allows repeating the following process tens of thousands of times: in the beginning CCD detects the image of the object with residual fluorescence. Then the image is digitized in a video-camera and is transmitted to computer. Then UV flash creates 1000-1600 fluorescing molecules in a vision area, and laser excites fluorescence in these molecules. CCD detects images of fluorescing molecules and particles, overlapped on residual fluorescence. The image is digitized in the video-camera and is transmitted to a computer where the previous frame with a residual fluorescence is subtracted from it. The received subtracted frame is stored in computer memory for further analysis with the purpose of calculating coordinates of a spot center, its averaged diameter, and intensity. Then the object is for some time lighted with laser without detecting its image to maximize color loss of already detected molecules. Then the whole cycle is repeated. New fluorescing molecules are created, detected and lose color in each cycle until coordinates of all dye molecules are detected. Molecular Probes produce not only mentioned dye. Dyes can be produced on request. It also produces sets of reagents for individual creating of such dyes, such as a "caging kit" (D-2516).

Cameras, indicated in the example, allow recording images of separate fluorescing molecules with a frequency of 10 frames per second. Images are recorded with satisfactory proportion of signal and noise. It is possible to detect, for example, 40000 frames during several hours. Each frame will contain up to 1600 images of molecules. If so, a total quantity of detected fluorescing molecules' coordinates can reach 64 million, an average distance between observed separately molecules can be only 10 nm. This is tens times better than in any other lens microscopes. Frames with molecule images should be saved without compressing or compressed without loosing quality. This should be done for more exact calculating of molecule coordinates. A total volume of information on all not compressed frames in one experiment can reach tens of gigabytes. This will not create a problem taking into account modern hard disk drives volume. Literature sources provide information on various algorithms of calculating spot centers. Computer software has been created to perform such calculations and reconstruction of a full image based on a table of calculated coordinates of spot centers.

What is claimed is:

1. A method for 3D microscopy of objects, comprising:
   introducing a fluorescent agent within an object;
   exciting the fluorescent agent;
   capturing with at least one camera and a data processor a plurality of image frames including separately observed fluorescing spots produced by the excited fluorescent agent;
   saving the captured image frames to a recordable medium associated with the data processor;
   obtaining more than one intensity distribution for each fluorescing spot from different focal planes with a light dividing prism and the at least one camera; and
   constructing a three-dimensional image of the object using differences between the light intensity distributions of each spot detected between the different focal planes.

2. The method of claim 1, further comprising introducing the fluorescent agent at a low concentration that allows the fluorescent agent to be detectable separately as spots when agent are excited.

3. The method of claim 1, wherein the light dividing prism and one or more cameras are positioned so neighboring focal planes of the object are projected through one object lens.

4. The method of claim 1, wherein the fluorescing spots correspond with lateral coordinates of the fluorescent agent.

5. The method of claim 1, wherein the fluorescent agent comprises fluorescent nanoparticles or fluorescent molecules.

6. The method of claim 1, wherein reconstructing the three-dimensional image comprises calculating an axial coordinate of each spot with an accuracy up to several nm.

7. The method of claim 1, wherein the fluorescent agent is a dye and the object is a dyed object, and further comprising:
   generating fluorescent molecules by converting non-fluorescent dye molecules into fluorescent dye molecules;
   exciting the fluorescent molecules of the dyed object, wherein each of the excited fluorescent molecules has a color; and
   registering each of the excited fluorescent molecules as the separate spot; and
   losing the color of the fluorescent molecules.

8. The method of claim 1, further comprising:
   introducing fluorescing nanoparticles as the fluorescent agent;
   registering a motion of the fluorescing nanoparticles resistant to fluorescent color loss within a portion of a sample filled with solution, the motion allowing a scan of accessible volume of the sample and to indicate volume that is filled with liquid and volume that is occupied with dense structures; and
   calculating a location of the nanoparticles from corresponding spots from all frames.

9. The method of claim 1, further comprising:
   repeating a cycle of the exciting and registering steps a plurality of times; and
   constructing a three-dimensional image of the object using differences between the light intensity distribution for each spot detected between the different focal planes over the cycle.

10. The method of claim 1, further comprising:
    introducing fluorescing nanoparticles as the fluorescent agent;
    registering a motion of the fluorescing nanoparticles resistant to fluorescent color loss within a portion of a sample filled with solution, the motion allowing a scan of accessible volume of the sample and to indicate volume that is filled with liquid and volume that is occupied with structures having the same local charge as the fluorescent agent; and
    calculating a location of the nanoparticles from corresponding spots from all frames.

11. The method of claim 1, further comprising determining lateral coordinates of the spots from the light intensity distributions of the plurality of focal planes.

12. The method of claim 1, wherein reconstructing the three-dimensional image comprises calculating an axial coordinate of each fluorescent agent spot.

* * * * *